US009918883B2

(12) United States Patent
Schroer, Jr.

(10) Patent No.: US 9,918,883 B2
(45) Date of Patent: *Mar. 20, 2018

(54) ABSORBENT ARTICLE HAVING A WETNESS INDICATOR

(71) Applicant: ASSOCIATED HYGIENIC PRODUCTS LLC, Duluth, GA (US)

(72) Inventor: Charles F. Schroer, Jr., Duluth, GA (US)

(73) Assignee: ASSOCIATED HYGIENIC PRODUCTS LLC, Duluth, GA (US)

( * ) Notice: Subject to any disclaimer, the term of this patent is extended or adjusted under 35 U.S.C. 154(b) by 312 days.

This patent is subject to a terminal disclaimer.

(21) Appl. No.: 14/687,795

(22) Filed: Apr. 15, 2015

(65) Prior Publication Data

US 2016/0067112 A1   Mar. 10, 2016

Related U.S. Application Data

(63) Continuation of application No. 11/751,963, filed on May 22, 2007, now Pat. No. 9,012,715.

(51) Int. Cl.
*A61F 13/42* (2006.01)
*A61F 13/84* (2006.01)

(52) U.S. Cl.
CPC ........ *A61F 13/42* (2013.01); *A61F 2013/421* (2013.01); *A61F 2013/422* (2013.01); *A61F 2013/425* (2013.01); *A61F 2013/426* (2013.01); *A61F 2013/8497* (2013.01)

(58) Field of Classification Search
CPC .......... A61F 2013/421; A61F 2013/422; A61F 2013/425; A61F 2013/8497
See application file for complete search history.

(56) References Cited

U.S. PATENT DOCUMENTS

| 4,022,211 A | 5/1977 | Timmons et al. ............ 604/361 |
| 4,292,916 A | 10/1981 | Bradley et al. ............... 116/205 |
| 4,812,053 A | 3/1989 | Bhattacharjee ............... 374/102 |
| 4,903,254 A | 2/1990 | Haas ............................. 368/327 |
| 4,940,464 A | 7/1990 | Van Gompel et al. ........ 604/396 |
| 4,987,849 A | 1/1991 | Sherman ....................... 116/206 |
| 5,045,283 A | 9/1991 | Patel ............................. 422/424 |
| 5,053,339 A | 10/1991 | Patel ................................. 436/2 |
| 5,058,088 A | 10/1991 | Haas et al. .................... 368/327 |
| 5,389,093 A | 2/1995 | Howell ......................... 604/361 |
| 5,435,010 A | 7/1995 | May .................................. 2/67 |
| 5,766,212 A | 6/1998 | Jitoe et al. .................... 604/361 |
| 5,766,389 A | 6/1998 | Brandon et al. ................ 156/64 |

(Continued)

FOREIGN PATENT DOCUMENTS

| EP | 1762209 | 3/2007 |
| WO | WO 2005/102238 | 11/2005 |
| WO | WO 2006/108002 | 10/2006 |

*Primary Examiner* — Susan Su
(74) *Attorney, Agent, or Firm* — Norton Rose Fulbright US LLP

(57) ABSTRACT

An absorbent article having an outer cover with an interior surface and an opposite exterior surface, an absorbent core positioned adjacent the interior surface of the outer cover, and a wetness indicator graphic located on the outer cover. The wetness indicator graphic has a permanent graphic defining at least one non-printed area and a changing graphic located within the at least one non-printed area of the permanent graphic such that the permanent graphic and the changing graphic together give the appearance of a uniform graphic.

19 Claims, 5 Drawing Sheets

(56) References Cited

U.S. PATENT DOCUMENTS

| | | |
|---|---|---|
| 6,297,424 B1 | 10/2001 | Olson et al. ................. 604/361 |
| 6,307,119 B1 | 10/2001 | Cammarota et al. ......... 604/361 |
| 6,596,918 B1 | 7/2003 | Wehrle et al. ................ 604/361 |
| 6,710,221 B1 | 3/2004 | Pierce et al. ................. 604/361 |
| 2003/0073966 A1 | 4/2003 | Sosalla et al. ............... 604/361 |
| 2005/0065489 A1 | 3/2005 | Driskell et al. .............. 604/361 |
| 2005/0234414 A1 | 10/2005 | Liu .............................. 604/361 |
| 2006/0003657 A1 | 1/2006 | Larson et al. ................ 442/327 |
| 2006/0004333 A1 | 1/2006 | Olson .......................... 604/361 |
| 2008/0132872 A1 | 6/2008 | Trennepohl et al. .... 604/385.24 |

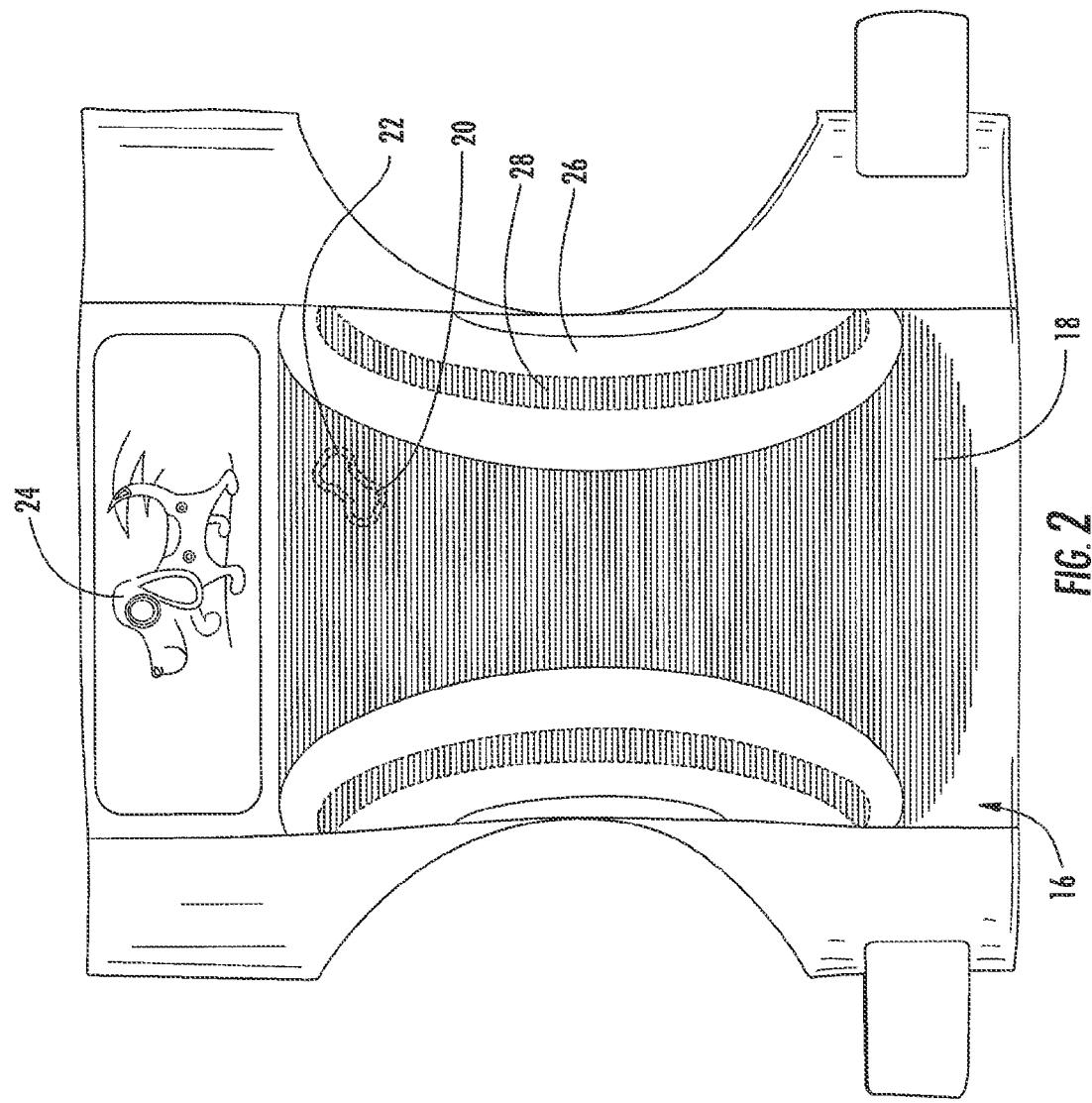

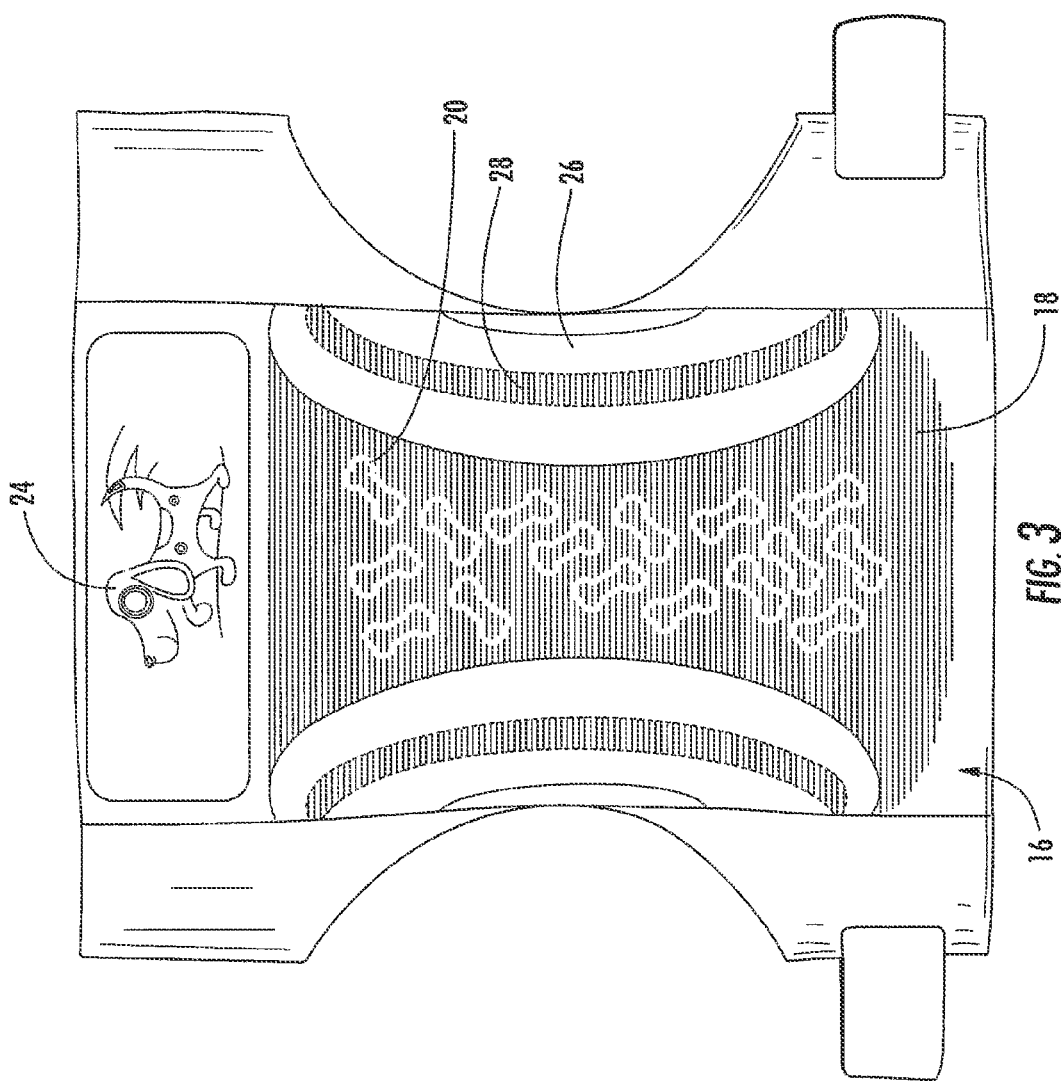

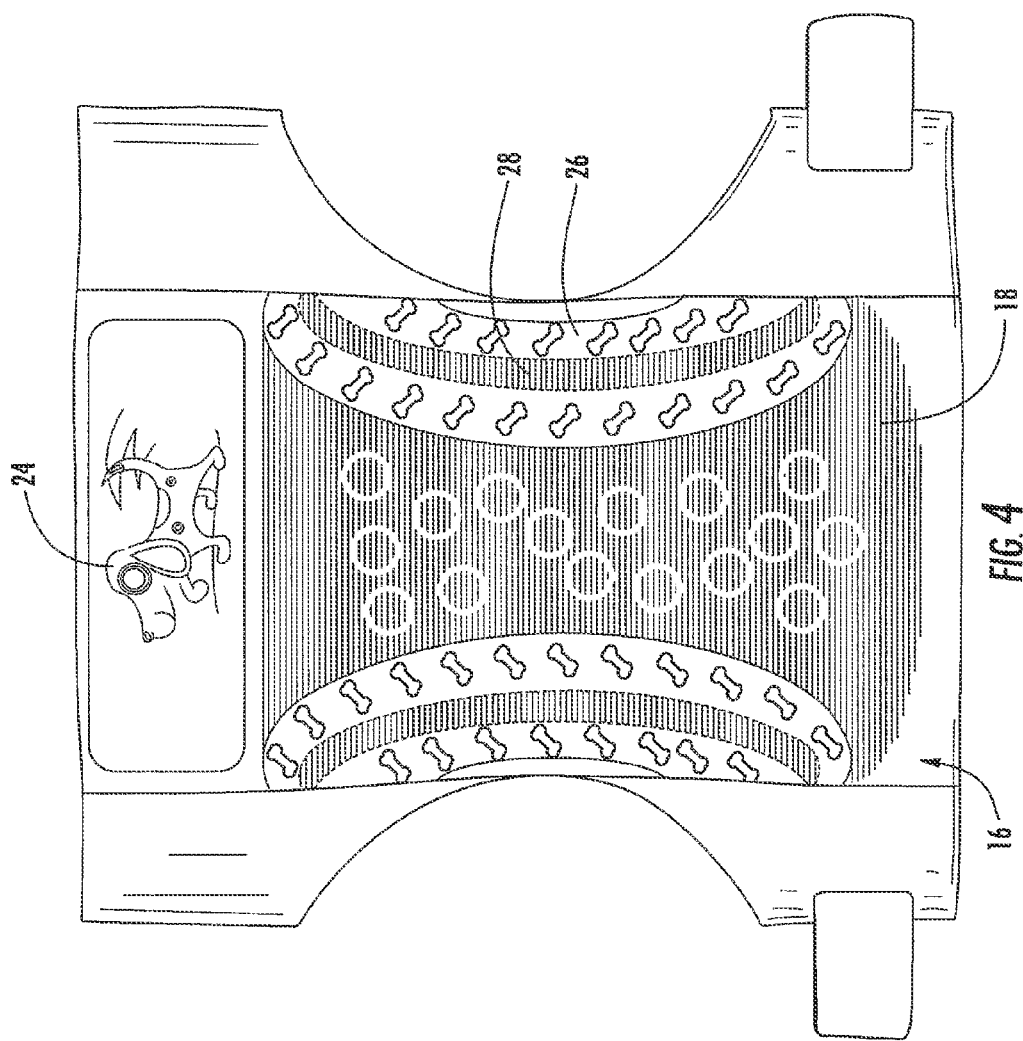

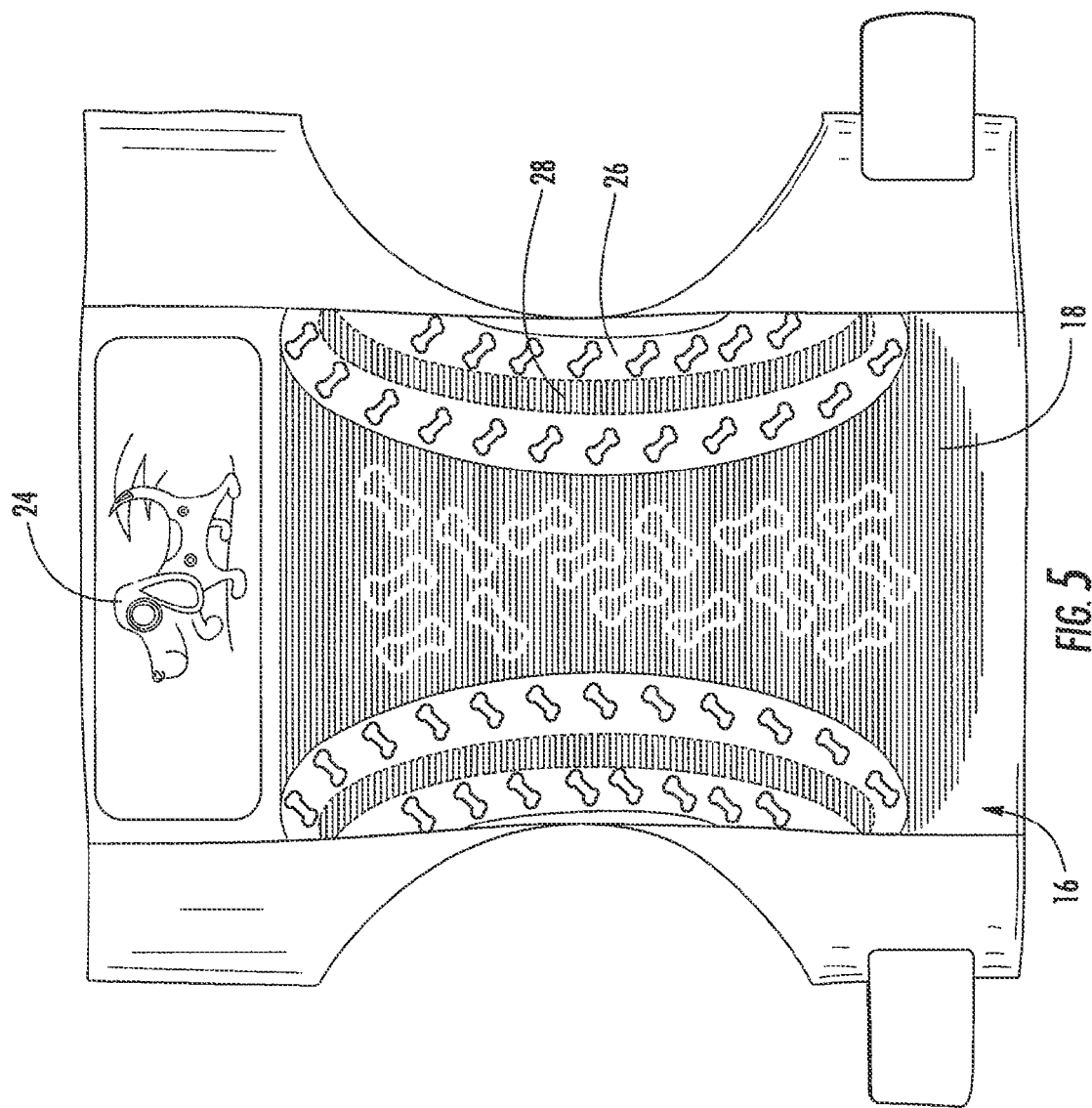

ABSORBENT ARTICLE HAVING A WETNESS INDICATOR

FIELD OF THE INVENTION

The present invention is directed to absorbent articles, and more particularly to absorbent articles with wetness indicators.

BACKGROUND OF THE INVENTION

Absorbent articles, for example, diapers or training pants, are commonly used to contain the incontinence of young Children. While diapers are traditionally drawn up between the legs and fastened about the waist, training pants are designed to give the appearance of underwear or apparel. Such training pants are often used to promote effective toilet training of children.

The toilet training of a young child typically includes a wide variety of training techniques and training aids that may be used by parents and caregivers. One technique of toilet training is to have the young child or caregiver recognize that the training pants are wet and in need of changing. This is best done by providing some form of graphical feedback to the child or caregiver to indicate that the training pants are wet. Accordingly, training pants are typically provided with readily visually perceptible wetness indicator graphics for specifically this purpose.

One of the problems with training pants and their associated wetness indicator graphics, however, is that they have the appearance of a diaper. Because of this, older children that are going through the toilet training process are often not amenable to or are uncomfortable wearing training pants reasoning that they are too old to wear diapers.

Such a reaction by a child can retard the toilet training process because the child may refuse to wear training pants altogether, and thus end up having "accidents" in their clothing.

SUMMARY OF THE INVENTION in order to address the aforementioned problems, the present invention provides an absorbent article, such as a diaper or training pants, that greater resembles the appearance of regular underwear or apparel while having a "hidden" wetness indicating graphic.

The purpose of the invention is to provide graphics for ornamental decoration of the absorbent article that do not noticeably appear to be a wetness indicator. The indication of wetness becomes noticeable after the article is soiled and results in a change in appearance of the graphics.

The absorbent article of the present invention improves significantly over the prior art absorbent articles by improving the appearance thereof to more closely resemble that of children's underwear. Specifically, the absorbent article of the present invention includes an outer cover having an interior surface and an opposite exterior surface, an absorbent core positioned adjacent the interior surface of the outer cover, and a wetness indicator graphic located between the outer cover and the absorbent core. The wetness indicator graphic has a permanent graphic defining at least one non-printed area, and a changing graphic located within the at least one non-printed area of the permanent graphic such that the permanent graphic and the changing graphic together give the appearance of a uniform graphic while the changing graphic is in a non-activated state. In other words, the changing graphic is hidden until such time as the article becomes soiled by the wearer.

The permanent graphic is preferably printed over a substantial portion of the outer cover using a permanent ink that does not change when in contact with moisture. The changing graphic is preferably printed within the non-printed areas defined by the permanent graphic using a suitable urine- or water-soluble ink and is configured to appear over time as the soluble ink fades when exposed to liquid. In addition to a moisture sensitive ink, the changing graphic can alternatively be printed using an ink that changes in response to time intervals, temperature levels, humidity, pH, oxygen levels, or the like, and any combinations thereof.

In the preferred embodiment, the permanent graphic and the hidden or changing graphic are printed in the same pattern and in the same color such that the permanent graphic and the changing graphic together, and prior to moisture contact, give the appearance of a uniform graphic. With such a construction, the absorbent article provides an overall appearance similar to that of actual children's underwear or apparel.

In addition to the wetness indicator graphic, the absorbent article preferably has a character graphic provided on the outer cover. To provide an overall theme to the absorbent article, it is preferred that the character graphic is be related to the design of the changing graphic (i.e., the shape of the non-printed area of the permanent graphic). Alternatively, the character graphic can also be unrelated to the design of the changing graphic (i.e., the shape of the non-printed area of the permanent graphic). As used herein the term "related to" refers to items, images or other indicia that are related by a common story line, related in subject matter, related by a common theme, complimentary images, or the same or a comparable image of different or similar size. For example, a character graphic of a dog would be related to a dog bone shape of the non-printed area of the permanent graphic.

In addition to the wetness indicator graphic and the character graphic, it is also preferred that the absorbent article include a seam pattern or other design on the outer cover as part of the permanent design. The seam pattern preferably has at least a portion thereof related to the wetness indicator graphic and/or the character graphic and can be gender specific or gender related.

Also disclosed is a method of manufacturing an absorbent article by providing an outer cover having an interior surface and an opposite exterior surface; disposing an absorbent core adjacent the interior surface of the outer cover; applying a barrier film having a printed permanent graphic on the outer cover, the permanent graphic defining at least one non-printed area; and printing a changing graphic within the at least one non-printed area of the permanent graphic such that the permanent graphic and the changing graphic are printed in complimentary patterns that together give the appearance of a uniform graphic.

BRIEF DESCRIPTION OF THE DRAWINGS

For the purpose of illustrating the invention, there is shown in the drawings a form which is presently preferred, it being understood, however, that the invention is not limited to the precise arrangement shown, wherein:

FIG. 2 is a top plan view of an absorbent article according to a first embodiment of the present invention and showing the permanent graphic defining at least one non-printed area indicating the shape of the changing graphic;

FIG. 3 is a top plan view of the absorbent article of FIG. 2, wherein the changing graphic is visible within the non-printed area;

FIG. 4 is a top plan view of an absorbent article according to a second embodiment of the present invention; and FIG. 5 is a top plan view of an absorbent article according to a third embodiment of the present invention.

DETAILED DESCRIPTION OF THE INVENTION

Figure 1:
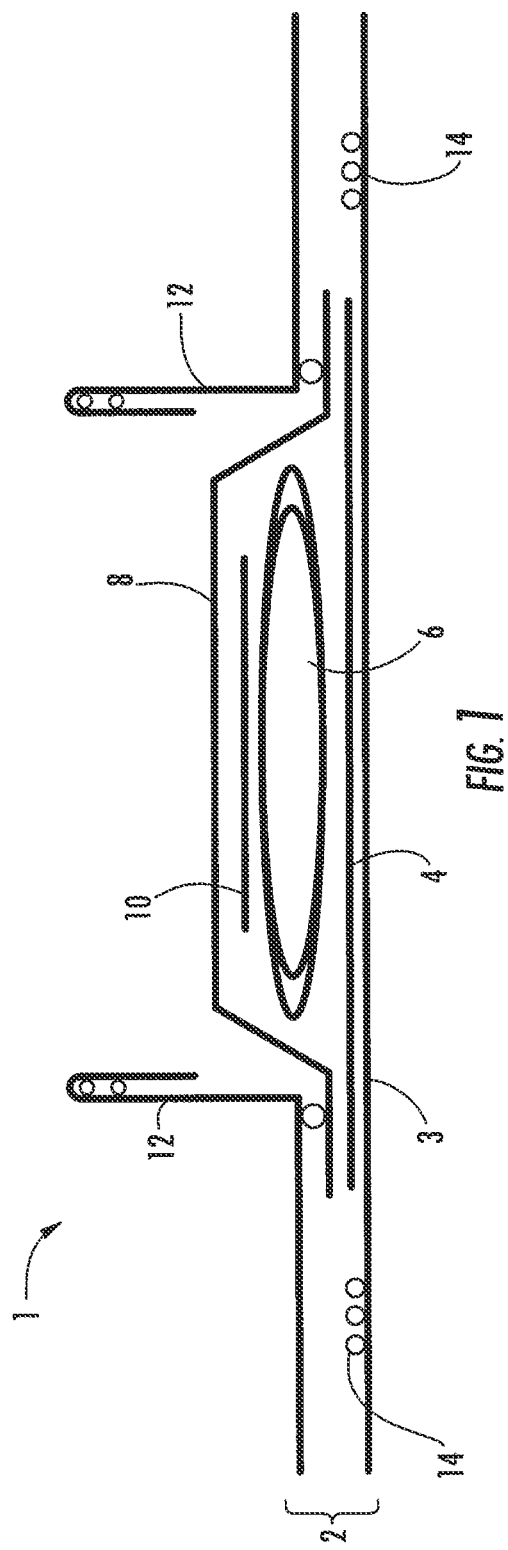
FIG. 1 is a cross-sectional view of an absorbent article according to a preferred embodiment of the present invention.

The present invention is directed to an absorbent article, such as a diaper or training pant, that is equipped with a wetness indicator graphic. Preferably, the absorbent article manufactured in accordance with the present invention is a disposable absorbent article in that the article is designed to be discarded after a limited use rather than being laundered or otherwise restored for reuse. The wetness indicator graphic of the present invention is a pattern, shape, etc. that either disappears or appears with moisture contact.

Referring now to the drawings, FIG. 1 is a cross-sectional view of an absorbent article 1 according to a first embodiment of the present invention. As Shown in FIG. 1, the absorbent article 1 includes an outer cover 2. In the preferred embodiment, the outer cover 2 includes a backsheet 3 and a barrier layer 4 adjacent an inner surface of the backsheet 2. The backsheet 2 and barrier layer 4 are preferably laminated, glued or otherwise attached together to form the outer cover 2 of the absorbent article 1. Preferably, the backsheet 2 is formed from a liquid permeable, non-woven material, and the barrier layer 4 is formed from a liquid impermeable poly sheet material. In alternate embodiments, the outer cover can be a single piece of liquid impermeable material, or multiple layers of permeable/non-permeable material, the choice of construction being left to the designer of the absorbent article.

As shown in FIG. 1, an absorbent core 6 is positioned adjacent to, and in liquid communication with, the barrier layer 4 of the outer cover 2. A topsheet 8 is positioned adjacent the absorbent core 6 such that the absorbent core 6 is located between the outer cover 2 and the topsheet 8. Preferably, the topsheet 8 is formed from a liquid permeable, non-woven material. In addition to the topsheet 8, the absorbent article 1 may also include an acquisition layer 10 between the topsheet 8 and the absorbent core 6. The use of an acquisition layer 10 assists in directing liquid exudates through the topsheet and into the absorbent core.

The absorbent article is also preferably provided with elasticized barrier cuffs 12 on opposed lateral sides of the absorbent core 6. The barrier cuffs 12 are typically bonded to the topsheet 8. The barrier cuffs 12 assist in preventing leakage of exudates from the leg opening portions of the absorbent article 1.

Leg elastics or leg gathers 14 are also preferably provided in the leg opening portions of the absorbent article 1. The leg elastics 14 assist in securing the absorbent article 1 around the legs of the wearer and also serve as a second containment structure beyond the barrier cuffs 12 to assist in preventing leakage through the leg opening portions of the absorbent article 1.

While FIG. 1 shows a preferred construction of the absorbent article according to the present invention, it will be readily apparent to one skilled in the art that other constructions and materials can be used. For example, the barrier cuff portions can be omitted and replaced with a single top sheet, the barrier cuffs can be bonded at different locations, etc.

In accordance with a first embodiment of the present invention shown in FIGS. 2 and 3, the outer cover 2 of the absorbent article 1 is provided with a wetness indicator graphic 16. Preferably, the wetness indicator graphic 16 is printed on the barrier layer 4 shown in FIG. 1 on the side thereof facing the absorbent core.

The wetness indicator graphic 16 includes a permanent graphic portion 18 defining at least one non-printed area 20, and a changing graphic portion 22 located within the at least one non-printed area 20. The permanent graphic 18 is preferably printed over a substantial portion of the outer cover 2 using a permanent ink that does not change when in contact with moisture. In the preferred embodiment shown in FIGS. 2 and 3, the non-printed areas 20 defined by the permanent graphic 18 are located in a crotch region of the absorbent article 1.

The changing graphic 22 is preferably printed within the non-printed areas 20 defined by the permanent graphic 18 using a suitable urine- or water-soluble ink so as to disappear over time due to exposure to liquid. Such inks are available from a variety of commercial vendors, such as Sun Chemical Corp. of Philadelphia, Pa., USA under the trade designation AQUA DESTRUCT™. In addition to a moisture sensitive ink, the changing graphic can alternatively be printed using an ink that changes in response to time intervals, temperature levels, humidity, oxygen levels, or the like, and any combinations thereof.

In the preferred embodiment, the permanent graphic 18 and the hidden or changing graphic 22 are printed in the same pattern and in the same color such that the permanent graphic 18 and the changing graphic 22 together, and prior to moisture contact, give the appearance of a uniform graphic as shown in FIG. 3. For illustration purposes only, FIG. 3 shows a non-printed area 20 in dotted lines to demonstrate how the permanent graphic 18 and the changing graphic 22 appear before moisture contact in the preferred embodiment. With such a construction, the absorbent article provides an overall appearance similar to that of actual children's underwear or apparel.

When the configuration of the permanent graphic 18 and the changing graphic 22 shown in FIG. 3 is exposed to wetness, the changing graphic 22 changes in accordance with the properties of the ink used, i.e., the changing graphic 22 washes away, changes color or fades, to expose the shape of the non-printed areas 20 of the permanent graphic 18. For example, if the changing graphic 22 is printed with ink that dissolves with moisture contact, the wetness indicator will appear as shown in FIG. 3 after moisture contact. Accordingly, when the pattern appears the child or caregiver can readily determine when the absorbent article is in need of changing.

Alternately, the changing graphic 22 can be printed with an ink that appears when contacted with moisture. In such an alteration, the absorbent article will display the shapes of the non-printed areas 20 before contact with moisture as shown for example in FIG. 2, and then the non-printed areas will "disappear" and a uniform graphic area will appear after contact with moisture. Thus, with such a modification, when the shapes of the non-printed areas disappear the child or caregiver can readily determine when the absorbent article is in need of changing.

In addition to the wetness indicator graphic 16, the absorbent article preferably has a character graphic 24 provided on the outer cover 2. The character graphic 24 can be provided on the outer cover 2 as a separately attached component, or can be printed directly on the outer cover 2.

To provide a theme to the absorbent article, it is preferred that the character graphic 24 is related to the design of the changing graphic (i.e., the shape of the non-printed areas 20 of the permanent graphic 18), as shown in FIGS. 2 and 3. For example, and as shown in FIG. 3, the character graphic 24 of a dog is related to the dog bone shape of the non-printed area 20 of the permanent graphic 18.

In addition to the wetness indicator graphic 16 and the character graphic 24, it is also preferred that the absorbent article include a seam pattern 26 or other design on the outer cover 2. Similar to the wetness indicator graphic 16, it is preferred that the seam pattern 26 or other design be printed on the barrier layer 4 of the outer cover 2.

As shown in FIGS. 2 and 3, the seam pattern 26 of the first embodiment has at least a portion thereof related to the wetness indicator graphic 16. For example, and as shown in FIGS. 2 and 3, the wetness indicator graphic 16 has both the permanent graphic 16 and the changing graphic 22 printed as a plurality of parallel lines, and the center portion 28 of the seam pattern 26 is printed with the same parallel line pattern. As such, the seam pattern 26 is related to the permanent graphic 18 and also the changing graphic 22.

Referring now to FIG. 4, a second embodiment of the present invention is shown. In contrast to the embodiment of FIG. 3, the character graphic shown in FIG. 4 is unrelated to the shape of the non-printed area of the permanent graphic. For example, in FIG. 4 the character graphic is a dog and the non-printed areas of the permanent graphic are circles. Similar to the first embodiment, a changing graphic (not-shown) is printed within the non-printed areas of the permanent graphic. The changing graphic can be configured to appear or disappear with moisture contact, etc.

Preferably, the permanent graphic and the changing graphic are printed in the same pattern and in the same color such that the permanent graphic and the changing graphic together, and prior to moisture contact, give the appearance of a uniform graphic so as to provide the absorbent article with an overall appearance similar to that of actual child underwear.

Moreover, the seam pattern shown in FIG. 4 has a portion with a dog bone design in addition to the other seam pattern graphics. Thus, in the second embodiment, at least a portion of the seam pattern is related to the character graphic.

FIG. 5 shows a third embodiment of the present invention wherein the character graphic is related to the shape of the non-printed area of the permanent graphic, and the seam pattern is in a shape related to the non-printed area of the permanent graphic. For example, in FIG. 5 the character graphic is a dog, the non-printed areas of the permanent graphic are shaped as dog bones and the seam pattern has a portion with a dog bone design in addition to the other seam pattern graphics. Thus, in the third embodiment, at least a portion of the seam pattern is related to the non-printed area of the permanent graphic as well as being related to the character graphic.

Similar to the first embodiment, a changing graphic (not-shown) is printed within the non-printed areas of the permanent graphic. Preferably, the permanent graphic and the changing graphic are printed in the same pattern and in the same color such that the permanent graphic and the changing graphic together, and prior to moisture contact, give the appearance of a uniform graphic.

Although the drawings herein show specific character graphics, non-printed area shapes and seam graphic combinations, there are a relatively unlimited number of possible combinations, the choice of which being left to the imagination of the designer of the absorbent article.

The present invention has been described in connection with the preferred embodiments. These embodiments, however, are merely examples and the invention is not restricted thereto. It will be understood by those skilled in the art that other variations and modifications can easily be made while remaining within the scope of the invention as defined by the appended claims.

What is claimed is:

1. An absorbent article comprising:
   an outer cover having an interior surface and an opposite exterior surface;
   an absorbent core positioned adjacent the interior surface of the outer cover; and
   a state change indicator graphic located on the outer cover, the state change indicator graphic comprising:
   a permanent graphic defining at least one non-printed area having a first shape; and
   a changing graphic located within the at least one non-printed area of the permanent graphic and having a second shape substantially similar to the first shape,
   wherein the permanent graphic cannot be differentiated from the changing graphic when the changing graphic is visually perceptible.

2. The absorbent article according to claim 1, wherein the changing graphic disappears at a certain temperature so as to reveal the non-printed area of the permanent graphic.

3. The absorbent article according to claim 1, wherein the changing graphic appears at a certain temperature.

4. The absorbent article according to claim 1, further comprising a character graphic.

5. The absorbent article according to claim 4, wherein the changing graphic disappears at a certain temperature so as to reveal the non-printed area, and the non-printed area is in a shape that is related to the character graphic.

6. The absorbent article according to claim 4, wherein the changing graphic disappears at a certain temperature so as to reveal the non-printed area, and the non-printed area is in a shape that is unrelated to the character graphic.

7. The absorbent article according to claim 1, further comprising a seam pattern located on the outer cover.

8. The absorbent article according to claim 7, wherein at least a portion of the state change indicator graphic is related to at least a portion of the seam pattern.

9. The absorbent article according to claim 7, wherein at least a portion of the permanent graphic is related to at least a portion of the seam pattern.

10. The absorbent article according to claim 7, wherein at least a portion of the changing graphic is related to at least a portion of the seam pattern.

11. The absorbent article according to claim 7, further comprising a character graphic.

12. The absorbent article according to claim 11, wherein at least a portion of the seam pattern is related to the character graphic.

13. The absorbent article according to claim 11, wherein the changing graphic disappears at a certain temperature so as to reveal the non-printed area, and the non-printed area is in a shape that is related to the character graphic.

14. The absorbent article according to claim 11, wherein the changing graphic disappears at a certain temperature so as to reveal the non-printed area, and the non-printed area is in a shape that is related to at least a portion of the seam patter.

15. The absorbent article according to claim 11, wherein the changing graphic disappears at a certain temperature so as to reveal the non-printed area, and the non-printed area is in a shape that is unrelated to the character graphic.

16. The absorbent article according to claim 1, wherein the permanent graphic and the changing graphic are substantially the same color before the certain temperature is reached.

17. The absorbent article according to claim 1, wherein the permanent graphic and the changing graphic are substantially the same color after the certain temperature is reached.

18. The absorbent article according to claim 1, wherein the permanent graphic and the changing graphic are different colors before certain temperature is reached.

19. The absorbent article according to claim 1, wherein the permanent graphic and the changing graphic are different colors after certain temperature is reached.

* * * * *